(12) United States Patent
Cao

(10) Patent No.: US 8,180,572 B2
(45) Date of Patent: May 15, 2012

(54) HIGH-RESOLUTION MELTING ANALYSIS

(75) Inventor: Weidong Cao, Rockville, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 651 days.

(21) Appl. No.: 12/257,713

(22) Filed: Oct. 24, 2008

(65) Prior Publication Data

US 2009/0112481 A1 Apr. 30, 2009

Related U.S. Application Data

(60) Provisional application No. 60/982,570, filed on Oct. 25, 2007.

(51) Int. Cl.
*G01N 33/48* (2006.01)
(52) U.S. Cl. ............ 702/19; 435/6; 435/7.1; 435/7.9; 435/91.1; 435/91.2; 544/245; 544/334; 544/242; 544/152; 536/23.1
(58) Field of Classification Search .......... 702/19; 435/6, 7.1, 4, 7.4, 91.1, 91.2, 7.9, 287.2, 435/283.1; 544/245, 276, 277, 334, 242, 544/152; 536/23.1, 23, 24.3
See application file for complete search history.

(56) References Cited

U.S. PATENT DOCUMENTS

| | | | |
|---|---|---|---|
| 6,174,670 B1 * | 1/2001 | Wittwer et al. ............... 435/6 |
| 6,960,437 B2 | 11/2005 | Enzelberger et al. |
| 7,122,321 B2 * | 10/2006 | Pantoliano et al. ............ 435/7.1 |
| 7,387,887 B2 * | 6/2008 | Wittwer et al. ............... 435/91.2 |
| 7,456,281 B2 * | 11/2008 | Dujols ........................... 544/242 |
| 7,582,429 B2 * | 9/2009 | Wittwer et al. ................ 435/6 |
| 7,781,165 B2 * | 8/2010 | Birkner et al. ................ 435/6 |
| 7,803,551 B2 * | 9/2010 | Wittwer et al. ............... 435/6 |
| 7,838,235 B2 * | 11/2010 | Caplin ......................... 435/6 |
| 7,910,720 B2 * | 3/2011 | Ankenbauer et al. ....... 536/24.33 |
| 2002/0197630 A1 | 12/2002 | Knapp et al. |
| 2005/0042639 A1 | 2/2005 | Knapp et al. |
| 2005/0059041 A1 * | 3/2005 | Johnson et al. ................ 435/6 |

(Continued)

FOREIGN PATENT DOCUMENTS

WO 2005075683 A1 8/2005

OTHER PUBLICATIONS

Lagally et al., "Single-Molecule DNA Amplificaton and Analysis in an Integrated Micofluidic Device," Analytical Chemistry, vol. 73, No. 3, (2001) pp. 565-570.

(Continued)

*Primary Examiner* — Carol Tsai
(74) *Attorney, Agent, or Firm* — Rothwell, Figg, Ernst & Manbeck, P.C.

(57) ABSTRACT

The present invention relates to methods and systems for the analysis of the dissociation behavior of nucleic acids and the identification of nucleic acids. In one aspect, methods and systems are disclosed for resolving a denaturation curve of a sample containing a first and second nucleic acid into a resolved denaturation curve for the first nucleic acid and a resolved denuration curve for the second nucleic acid.

18 Claims, 5 Drawing Sheets

U.S. PATENT DOCUMENTS

| | | |
|---|---|---|
| 2005/0233335 A1 | 10/2005 | Wittwer et al. |
| 2006/0019253 A1 | 1/2006 | Wittwer et al. |
| 2007/0020672 A1* | 1/2007 | Wittwer et al. .................. 435/6 |
| 2007/0026421 A1* | 2/2007 | Sundberg et al. ................ 435/6 |
| 2007/0161020 A1* | 7/2007 | Luo et al. ......................... 435/6 |
| 2007/0231799 A1 | 10/2007 | Knight et al. |
| 2009/0075269 A1* | 3/2009 | Caplin .............................. 435/6 |

OTHER PUBLICATIONS

Kopp et al., "Chemical Amplification: Continuous-Flow PCR on a Chip," Science, vol. 280, (1998) pp. 1046-1048.

Park et al., "Cylindrical compact thermal-cycling device for continuous-flow polymerase chain reaction," Analytical Chemistry, vol. 75 (2003) pp. 6029-6033.

* cited by examiner

HIGH-RESOLUTION MELTING ANALYSIS

CROSS-REFERENCE TO RELATED APPLICATION

This application claims the benefit of U.S. Provisional Patent Application Ser. No. 60/982,570, filed on Oct. 25, 2007, which is incorporated herein by reference in its entirety.

BACKGROUND

1. Field of the Invention

The present invention relates to methods and systems for the analysis of the dissociation behavior of nucleic acids and the identification of nucleic acids. More specifically, embodiments of the present invention relate to methods and systems for the analysis of denaturation data of nucleic acids.

2. Description of Related Art

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. PCR is perhaps the most well-known of a number of different amplification techniques.

PCR is a powerful technique for amplifying short sections of DNA. With PCR, one can quickly produce millions of copies of DNA starting from a single template DNA molecule. PCR includes a three phase temperature cycle of denaturation of DNA into single strands, annealing of primers to the denatured strands, and extension of the primers by a thermostable DNA polymerase enzyme. This cycle is repeated so that there are enough copies to be detected and analyzed. In principle, each cycle of PCR could double the number of copies. In practice, the multiplication achieved after each cycle is always less than 2. Furthermore, as PCR cycling continues, the buildup of amplified DNA products eventually ceases as the concentrations of required reactants diminish. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

Real-time PCR refers to a growing set of techniques in which one measures the buildup of amplified DNA products as the reaction progresses, typically once per PCR cycle. Monitoring the accumulation of products over time allows one to determine the efficiency of the reaction, as well as to estimate the initial concentration of DNA template molecules. For general details concerning real-time PCR see *Real-Time PCR: An Essential Guide*, K. Edwards et al., eds., Horizon Bioscience, Norwich, U.K. (2004).

More recently, a number of high throughput approaches to performing PCR and other amplification reactions have been developed, for example, involving amplification reactions in microfluidic devices, as well as methods for detecting and analyzing amplified nucleic acids in or on the devices. Thermal cycling of the sample for amplification in microfluidic devices is usually accomplished in one of two methods. In the first method, the sample solution is loaded into the device and the temperature is cycled in time, much like a conventional PCR instrument. In the second method, the sample solution is pumped continuously through spatially varying temperature zones. See, e.g., Lagally et al. (*Analytical Chemistry* 73:565-570 (2001)), Kopp et al. (*Science* 280:1046-1048 (1998)), Park et al. (*Analytical Chemistry* 75:6029-6033 (2003)), Hahn et al. (WO 2005/075683), Enzelberger et al. (U.S. Pat. No. 6,960,437) and Knapp et al. (U.S. Patent Application Publication No. 2005/0042639).

Once there are a sufficient number of copies of the original DNA molecule, the DNA can be characterized. One method of characterizing the DNA is to examine the DNA's dissociation behavior as the DNA transitions from double stranded DNA (dsDNA) to single stranded DNA (ssDNA) with increasing temperature. The process of causing DNA to transition from dsDNA to ssDNA is sometimes referred to as a "high-resolution temperature (thermal) melt (HRTm)" process, or simply a "high-resolution melt" process.

Melt curve analysis is an important technique for analyzing nucleic acids. In accordance with some methods, a double stranded nucleic acid is denatured in the presence of a dye that indicates whether the two strands are bound or not. Examples of such indicator dyes include non-specific binding dyes such as SYBR® Green I, whose fluorescence efficiency depends strongly on whether it is bound to double stranded DNA. As the temperature of the mixture is raised, a reduction in fluorescence from the dye indicates that the nucleic acid molecule has melted, i.e., unzipped, partially or completely. Thus, by measuring the dye fluorescence as a function of temperature, information is gained regarding the length of the duplex, the GC content or even the exact sequence. See, e.g., Ririe et al. (*Anal Biochem* 245:154-160, 1997), Wittwer et al. (Clin Chem 49:853-860, 2003), Liew et al. (Clin Chem 50:1156-1164 (2004), Herrmann et al. (Clin Chem 52:494-503, 2006), Knapp et al. (U.S. Patent Application Publication No. 2002/0197630), Wittwer et al. (U.S. Patent Application Publication No. 2005/0233335), Wittwer et al. (U.S. Patent Application Publication No. 2006/0019253), Sundberg et al. (U.S. Patent Application Publication No. 2007/0026421) and Knight et al. (U.S. Patent Application Publication No. 2007/0231799).

Some nucleic acid assays require identification of a single nucleotide change where the difference in melting temperature ($T_m$) between the wild type nucleic acid and the mutant nucleic acid is less than, for example, 0.25° C. This level of temperature resolution is difficult, if not impossible, in standard 96 and 384 well plates. Decreasing the area of thermal analysis can improve the spatial temperature gradient, but there is still significant noise generated from the heating device used to linearly ramp the samples during a thermal melt. Accordingly, what are desired are methods and systems for high resolution melt analysis that are capable of more accurately discriminating thermal melt curves and obtaining DNA sequence information from these melting curves, especially where these thermal melt curves are differentiated by a small temperature range.

SUMMARY OF THE INVENTION

The present invention relates to methods and systems for the analysis of the dissociation behavior of nucleic acids and the identification of nucleic acids. More specifically, embodiments of the present invention relate to methods and systems for the analysis of denaturation data of nucleic acids.

In one aspect, the present invention provides a method of resolving a denaturation curve of a sample containing a first and second nucleic acid into a resolved denaturation curve for the first nucleic acid and a resolved denaturation curve for the second nucleic acid. According to this aspect, the method comprises deriving or plotting a denaturation curve from denaturation data and calculating an estimated intrinsic physical value associated with the first nucleic acid by using data from a non-overlapping region of the denaturation curve. The method further comprises calculating a first resolved denaturation curve for the first nucleic acid using the estimated intrinsic physical value, and subtracting the first resolved denaturation curve for the first nucleic acid from the denaturation curve to generate a second resolved denaturation curve for the second nucleic acid. In one embodiment, the method further comprises the step of determining the melting temperatures ($T_m$s) from the resolved melting curves.

In one embodiment, the denaturation data includes measurements of a quantifiable physical change P of the sample at a plurality of independent sample property points x. In another embodiment, the quantifiable physical change P is associated with denaturation of a nucleic acid. In a further embodiment, the plurality of independent sample property points x are a plurality of temperatures. In one embodiment, the intrinsic physical property is the enthalpy of denaturation of the first nucleic acid. In another embodiment, the method further comprises calculating the van't Hoff enthalpy of the first nucleic acid by using data from the non-overlapping region of the denaturation curve. In a further embodiment, the method further comprises the step of determining an estimated van't Hoff enthalpy and entropy change of the second nucleic acid from the resolved denaturation curve for the second nucleic acid.

In another embodiment, the method further comprises the step of determining the melting temperature of the first nucleic acid from the resolved melting curve for the first nucleic acid, and determining the melting temperature of the second nucleic acid from the resolved denaturation curve for the second nucleic acid. In another embodiment, the sample further includes a double-strand specific fluorescent dye. In a further embodiment, the quantifiable physical change is the fluorescence intensity. In one embodiment, the first nucleic acid and second nucleic acid are single nucleotide polymorphisms of one another. In another embodiment, the method further comprises the step of generating denaturation data including measurements of a quantifiable physical change P of the sample at a plurality of independent sample property points x for a sample. In a further embodiment, the quantifiable physical change P is associated with denaturation of a nucleic acid. In one embodiment, the denaturation data is thermal melt data.

In another aspect, the present invention provides a system for resolving a denaturation curve of a sample containing a first nucleic acid and a second nucleic acid into a resolved melt curve for the first nucleic acid and a resolved melt curve for the second nucleic acid. In accordance with this aspect, the system comprises a plotting module capable of plotting a denaturation curve from denaturation data and an estimating module capable of calculating an estimated intrinsic physical value associated with the first nucleic acid by using data from a non-overlapping region of a denaturation curve. The system further comprises a resolving module capable of calculating a resolved denaturation curve for the first nucleic acid using the estimated intrinsic physical value, and subtracting the first resolved denaturation curve for the first nucleic acid from a denaturation curve to generate a second resolved denaturation curve for the second nucleic acid.

In one embodiment of the system for resolving a denaturation curve, the denaturation data includes measurements of a quantifiable physical change P of the sample at a plurality of independent sample property points x. In another embodiment, the quantifiable physical change P is associated with the denaturation of a nucleic acid. In a further embodiment, the plurality of independent sample property points x are a plurality of temperatures. In one embodiment, the intrinsic physical property is the enthalpy of denaturation of the first nucleic acid. In another embodiment, the estimating module is further capable of calculating the van't Hoff enthalpy of the first nucleic acid by using data from the non-overlapping region of the denaturation curve. In a further embodiment, the system further comprises a thermodynamic information determining module capable of determining an estimated van't Hoff enthalpy and entropy change of the second nucleic acid from the second resolved denaturation curve for the second nucleic acid.

In yet another embodiment, the system further comprises a melting temperature determining module capable of determining the melting temperature of the first nucleic acid from the resolved denaturation curve for the first nucleic acid, and determining the melting temperature of the second nucleic acid from the resolved denaturation curve for the second nucleic acid. In another embodiment, the sample further includes a double-strand specific fluorescent dye. In a further embodiment, the quantifiable physical change is the fluorescence intensity. In one embodiment, the first nucleic acid and second nucleic acid are single nucleotide polymorphisms of one another. In another embodiment, the system further comprises a generating unit capable of generating denaturation data including measurements of a quantifiable physical change P of the sample at a plurality of independent sample property points x for a sample. In a further embodiment, the quantifiable physical change P is associated with denaturation of a nucleic acid. In one embodiment, the denaturation data is thermal melt data.

BRIEF DESCRIPTION OF THE FIGURES

The accompanying drawings, which are incorporated herein and form part of the specification, illustrate various embodiments of the present invention.

DETAILED DESCRIPTION OF PREFERRED EMBODIMENTS

Figure 1:
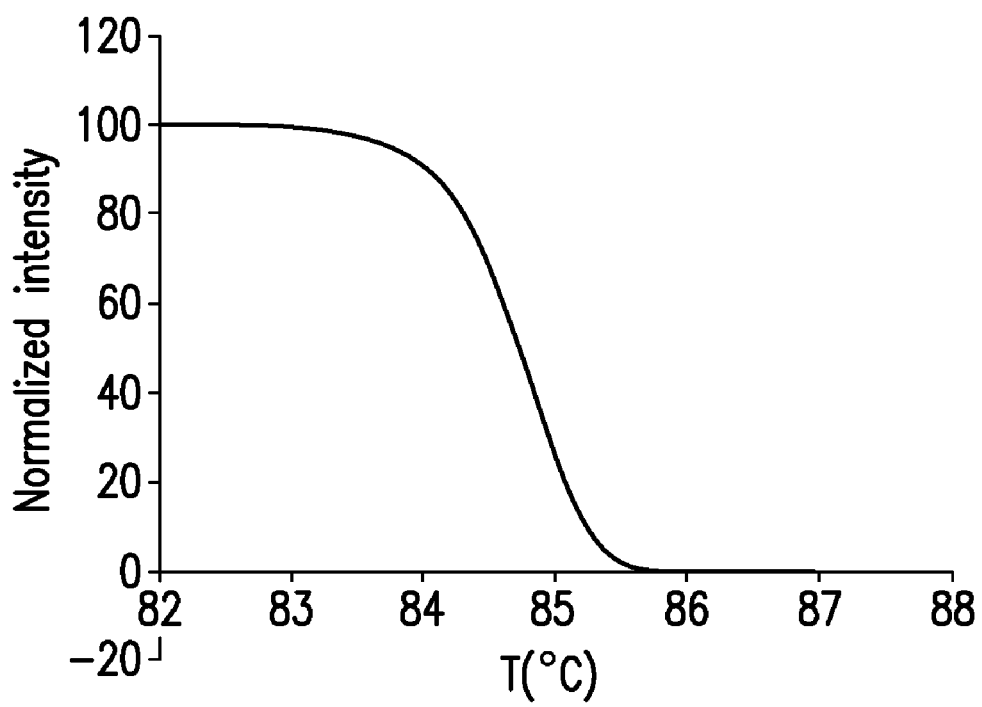
FIG. 1 illustrates a melting curve of a wild type DNA PCR product.

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, N.Y., Gait, *Oligonucleotide Synthesis: A Practical Approach,* 1984, IRL Press, London, Nelson and Cox (2000), Lehninger, *Principles of Biochemistry* 3rd Ed., W. H. Freeman Pub., New York, N.Y. and Berg et al. (2002) *Biochemistry,* 5th Ed., W. H. Freeman Pub., New York, N.Y., all of which are herein incorporated in their entirety by reference for all purposes.

Thermal melt curves of fluorescence have been used to determine the melting temperature of a DNA strand when denatured from the duplex state to the two separate single strands via a ramp increase in temperature. Typically, the melting temperature or $T_m$ is defined to be the temperature at which 50% of the paired DNA strands have denatured into single strands. Intercalating dyes that fluoresce when bound to double stranded DNA and lose there fluorescence when denatured are often used in measuring $T_m$. Typically, the negative derivative of fluorescence with respect to temperature ($-dF/dT$) has been used in the determination of $T_m$. In typical systems, the temperature at the peak $-dF/dT$ is used as an estimate of the melting temperature $T_m$.

The $-dF/dT$ derivative curve is typically obtained using a Savitsky-Golay (SG) derivative filter which is capable of estimating the derivative of any signal. Savitsky-Golay filters are low pass, Finite Impulse Response (FIR) derivative filters, and their application to any dynamical signal is obtained through the convolution of the FIR filter parameters with the raw signal. When the spacing of the independent variable is uniform, the filtered results can give first order and higher order derivatives of the dependant variable relative to the independent variable equivalent. The effect of such a filter is equivalent to a moving polynomial fit, followed by the evaluation of the derivative of that polynomial evaluated at the center of the window. To use the SG filter the temperature difference between consecutive points has to be exactly equal (perfect ramp in temperature), otherwise there are potential problems, such as the lowering and broadening of peaks, due to the low pass filtering effect of the SG filter. Furthermore, the degree of filtering depends on the polynomial order and window size (or number of points). In the frequency domain, sharper peaks are further attenuated than broader ones. Perhaps the greatest shortcoming of the SG derivative filter is its inability to resolve and detect multiple melting temperatures for heterozygous mutant DNA when there are two or more $T_m$ temperatures that are in close proximity.

In one aspect of the present invention, methods and systems are described that do not suffer from the shortcomings of using SG derivative filters and that have the ability to detect one or more melting temperature(s) from DNA thermal melt data as well as other thermodynamic parameters for each melting temperature.

In addition, when the melting temperatures between the wild type nucleic acid and the mutant nucleic acid are close enough, an overlap will be formed between two derivative melting curves, e.g., the derivative melting curves that are obtained for the wild type allele and the mutant allele in a heterozygous sample. Such an overlap in the derivative melting curves can effect the measurement of the melting temperature. In other aspects of the present invention, methods and systems are described that resolve the melting curves to precisely measure the melting temperatures of the alleles present in the sample.

The present invention relates to methods and systems for the analysis of the dissociation behavior of nucleic acids and the identification of nucleic acids. More specifically, the present invention relates to methods and systems for the analysis of denaturation data of nucleic acids and the identification of nucleic acids. For example, melting curve analysis can be used to detect single nucleotide polymorphisms (SNPs). Molecular melt curves (and differences between molecular melt curves) can also be used to detect and analyze sequence differences between nucleic acids. The thermal denaturation curve for nucleic acids can be monitored by, for example, measuring thermal parameters, fluorescence of indicator dyes/molecules, fluorescence polarization, dielectric properties, or the like.

Melting curve analysis is typically carried out either in a stopped flow format or in a continuous flow format. In one example of a stopped flow format, flow is stopped within a microchannel of a microfluidic device while the temperature in that channel is ramped through a range of temperatures required to generate the desired melt curve. In an alternative stopped flow format, melting curve analysis is done in a chamber to which the nucleic acid sample has been added. In one example of a continuous flow format, a melting curve analysis is performed by applying a temperature gradient along the length (direction of flow) of a microchannel of a microfluidic device. If the melting curve analysis requires that the molecules being analyzed be subjected to a range of temperatures extending from a first temperature to a second temperature, the temperature at one end of the microchannel is controlled to the first temperature, and the temperature at the other end of the length is controlled to the second temperature, thus creating a continuous temperature gradient spanning the temperature range between the first and second selected temperatures. An example of an instrument for performing a melting curve analysis is disclosed in U.S. Patent Application Publication No. 2007/0231799, incorporated herein by reference in its entirety.

The denaturation data that is analyzed in accordance with aspects of the present invention is obtained by techniques well known in the art. See, e.g., Knight et al. (U.S. Patent Application Publication No. 2007/0231799); Knapp et al. (U.S. Patent Application Publication No. 2002/0197630); Wittwer et al. (U.S. Patent Application Publication No. 2007/0020672); and Wittwer et al. (U.S. Pat. No. 6,174,670). Although the present invention is applicable to the analysis of denaturation data obtained in any environment, it is particularly useful for denaturation data obtained in the microfluidic environment because of the need for greater sensitivity in this environment.

In accordance with certain aspects of the invention, thermal melt data is generated by elevating the temperature of a molecule or molecules, e.g., of one or more nucleic acids, for a selected period of time and measuring a detectable property emanating from the molecule or molecules, wherein the detectable property indicates an extent of denaturation of the nucleic acid. This period of time can range, for example, from about 0.01 second through to about 1.0 minute or more, from about 0.01 second to about 10 seconds or more, or from about 0.1 second to about 1.0 second or more, including all time periods in between. In one embodiment, heating comprises elevating the temperature of the molecule or molecules by continuously increasing the temperature of the molecule or molecules. For example, the temperature of the molecule(s) can be continuously increased at a rate in the range of about 0.1° C./second to about 1° C./second. Alternatively, the temperature of the molecule(s) can be continuously increased at a slower rate, such as a rate in the range of about 0.01° C./second to about 0.1° C./second, or at a faster rate, such as a rate in the range of about 1° C./second to about 10° C./second. The heating can occur through application of an internal or an external heat source, as is known in the art.

The actual detection of a change(s) in a physical property of the molecules can be detected in numerous methods depending on the specific molecules and reactions involved. For example, the denaturation of the molecules can be tracked by following fluorescence or emitted light from molecules in the assay. The degree of, or change in, fluorescence is correlational or proportional to the degree of change in conformation of the molecules being assayed. Thus, in some methods, the detection of a property of the molecule(s) comprises detecting a level of fluorescence or emitted light from the molecules(s) that varies as a function of relative amounts of binding. In one configuration, the detecting of fluorescence involves a first molecule and a second molecule, wherein the first molecule is a fluorescence indicator dye or a fluorescence indicator molecule and the second molecule is the target molecule to be assayed. In one embodiment, the fluorescence indicator dye or fluorescence indicator molecule binds or associates with the second molecule by binding to hydrophobic or hydrophilic residues on the second molecule. The methods of detecting optionally further comprise exciting the fluorescence indicator dye or fluorescence indicator molecule to create an excited fluorescence indicator dye or excited fluorescence indicator molecule and discerning and measuring an emission or quenching event of the excited fluorescence indicator dye or fluorescence indicator molecule.

In aspects of the present invention, the thermal melt data can be used to generate a thermal property curve. In some methods, the generation of a thermal property curve includes providing one molecule comprising a fluorescence indicator dye or fluorescence indicator molecule, and at least a second molecule comprising, one or more of an enzyme, a ligand, a peptide nucleic acid, a cofactor, a receptor, a substrate, a protein, a polypeptide, a nucleic acid (either double-stranded or single-stranded), an antibody, an antigen, or an enzyme complex. Fluorescence of the first molecule in the presence of the second molecule as a function of temperature is measured and the resulting data is used to generate a thermal property curve. In other methods, the generation of a thermal property curve comprises measuring a change in the fluorescence of one molecule that is correlative or proportional to a change in a physical property of another molecule(s) due to a change in temperature. In still other methods, the generation of a thermal property curve comprises measuring the change in the total free energy of the system as a function of temperature without the presence of a second molecule. Typically, the methods also include generating a thermal property curve of a control or known sample in a similar manner.

Several techniques exist for the measurement of the denaturation of the molecules of interest, and any of these can be used in generating the data to be analyzed in accordance with aspects of the present invention. Such techniques include fluorescence, fluorescence polarization, fluorescence resonance energy transfer, circular dichroism and UV absorbance. Briefly, the fluorescence techniques involves the use of spectroscopy to measure changes in fluorescence or light to track the denaturation/unfolding of the target molecule as the target molecule is subjected to changes in temperature. Spectrometry, e.g. via fluorescence, is a useful method of detecting thermally induced denaturation/unfolding of molecules. Many different methods involving fluorescence are available for detecting denaturation of molecules (e.g. intrinsic fluorescence, numerous fluorescence indicator dyes or molecules, fluorescence polarization, fluorescence resonance energy transfer, etc.) and are optional embodiments of the present invention. These methods can take advantage of either internal fluorescent properties of target molecules or external fluorescence, i.e. the fluorescence of additional indicator molecules involved in the analysis.

A method of measuring the degree of denaturation/unfolding of the target molecule is through monitoring of the fluorescence of dyes or molecules added to the microfluidic device along with the target molecule and any test molecules of interest. A fluorescence dye or molecule refers to any fluorescent molecule or compound (i.e., a fluorophore) which can bind to a target molecule either once the target molecule is unfolded or denatured or before the target molecule undergoes conformational change by, e.g., denaturing and which emits fluorescent energy or light after it is excited by, e.g., light of a specified wavelength.

One dye type used in the microfluidic devices is one that intercalates within strands of nucleic acids. The example of such a dye is ethidium bromide. An example of use of ethidium bromide for binding assays includes, e.g., monitoring for a decrease in fluorescence emission from ethidium bromide due to binding of test molecules to nucleic acid target molecules (ethidium bromide displacement assay). See, e.g., Lee, M. et al. (*J Med Chem* 36(7):863-870 (1993)). The use of nucleic acid intercalating agents in measurement of denaturation is well known to those in the art. See, e.g., Haugland (*Handbook of Fluorescent Probes and Research Chemicals*, Molecular Probes, Inc., Eugene, Oreg. (1996)).

Dyes that bind to nucleic acids by mechanisms other than intercalation can also be employed in embodiments of the invention. For example, dyes that bind the minor groove of double stranded DNA can be used to monitor the molecular unfolding/denaturation of the target molecule due to temperature. Examples of suitable minor groove binding dyes are the SYBR Green family of dyes sold by Molecular Probes Inc. (Eugene, Oreg., USA). See, e.g., Haugland (*Handbook of Fluorescent Probes and Research Chemicals*, Molecular Probes, Inc., Eugene, Oreg., USA (1996)). SYBR Green dyes will bind to any double stranded DNA molecule. When a SYBR Green dye binds to double stranded DNA, the intensity of the fluorescent emissions increases. As more double stranded DNA are denatured due to increasing temperature, the SYBR Green dye signal will decrease. Another suitable dye is LCGreen Plus sold by Idaho Technology, Inc. (Salt Lake City, Utah, USA).

Fluorescence polarization (FP) provides a useful method to detect hybridization formation between molecules of interest. This method is especially applicable to hybridization detection between nucleic acids, for example, to monitor single nucleotide polymorphisms (SNPs). Generally, FP operates by monitoring, the speed of rotation of fluorescent labels, such as fluorescent dyes or molecular beacons, e.g. before, during, and/or after binding events between molecules that comprise the test and target molecules. In short, binding of a test molecule to the target molecule ordinarily results in a decrease in the speed of rotation of a bound label on one of the molecules, resulting in a change in FP.

Fluorescence resonance energy transfer (FRET) can be used to track the conformational changes of the target molecule (and interactions with test molecules which can bind with the target molecule) as a function of temperature. FRET relies on a distance-dependent transfer of energy from a donor fluorophore to an acceptor fluorophore. If an acceptor fluorophore is in close proximity to an excited donor fluorophore then the emission of the donor fluorophore can be transferred to the acceptor fluorophore. This causes a concomitant reduction in the emission intensity of the donor fluorophore and an increase in the emission intensity of the acceptor fluorophore. Since the efficiency of the excitation transfer depends, inter alia, on the distance between the two fluorophores, the technique can be used to measure extremely small distances such as would occur when detecting changes in conformation. This technique is particularly suited for measurement of binding reactions, protein-protein interactions, e.g., such as a protein of interest binding to an antibody and other biological events altering the proximity of two labeled molecules. Many appropriate interactive labels are known. For example, fluorescent labels, dyes, enzymatic labels, and antibody labels are all appropriate.

Circular dichroism (CD) can be used to follow the conformational changes of the target molecules/text molecules as a function of temperature and can be used to construct molecular melt curves. CD is a type of light absorption spectroscopy which measures the difference in absorbance by a molecule between right-circularly polarized light and left-circularly polarized light. CD is quite sensitive to the structure of polypeptides and proteins.

UV absorbance can also be used to detect and/or track denaturation of nucleic acid molecules, and/or to quantify the total amount of nucleic acid. UV can be employed to measure the extent of denaturation because the UV absorbance value of single stranded nucleic acid molecules is greater than the absorbance value of double stranded nucleic acid molecules.

Once the denaturation data has been obtained and melt curves generated, if desired, the data and/or melt curves are then analyzed to identify the molecules in the sample, such as, for example, the identification of a nucleic acid in a sample. This analysis is performed in accordance with the aspects of the present invention which are described herein.

In one aspect, the invention provides methods for resolving a denaturation curve of a sample containing a first and second nucleic acid into a resolved denaturation curve for the first nucleic acid and a resolved denaturation curve for the second nucleic acid. It is recognized that when the melting temperatures of a mutant nucleic acid and a wild type nucleic acid are close, an overlap will be formed between the two derivative melting curves, which can effect the measurement of the melting temperature. This aspect of the invention resolves the curves so that DNA sequence information can be obtained.

In addition, this aspect of the invention offers a method of calculating nucleic acid melting enthalpy and entropy from a nucleic acid melting curve. In accordance with this aspect, the nucleic acid melting enthalpy and entropy is calculated from a known wild type melting curve. By assuming that the wild type DNA entropy is the same as that in the SNP curve and using the non-overlapped part of melting curve, enthalpy of the wild type in the SNP can be calculated out from melting curve. Therefore, the whole wild type melting curve can be determined by the entropy and enthalpy. In one embodiment, by subtracting the wild type melting curve from the SNP melting curve, the mutated (i.e. SNP) DNA melting curve, is determined. Therefore, the melting temperature can be easily and accurately measured from resolved melting curve.

Figure 2:
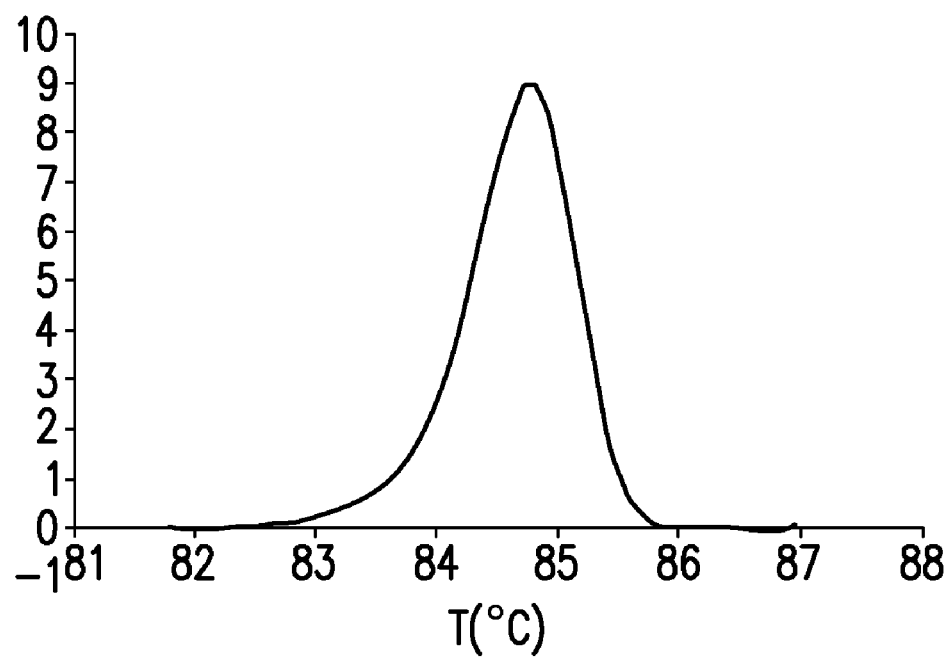
FIG. 2 illustrates a derivative melting curve of the melting curve in FIG. 1 of a wild type DNA PCR product.

FIGS. 1 and 2 represent an example of a melting curve and its derivative melting curve of a wild type DNA PCR product. According to one embodiment, enthalpy and entropy are calculated from melting curve using the following method based on thermodynamic relationship:

$$\Delta H = \frac{T1 T2 R \ln(K1/K2)}{T1 - T2}, k = \frac{2\alpha}{(1-\alpha)^2 C0}$$

wherein T1, T2 is temperature, $\alpha$ is the ratio of ds-DNA in total DNA and C0 is total DNA. Using this equation, a rough $\Delta H$ value can be calculated from the melting curve. Then, entropy can be calculated by the equation:

$$\Delta S = \frac{\Delta H}{Tm} + R\ln(4/C0).$$

The calculated entropy is then used in the following equation:

$$\Delta H - T \Delta S = RT \ln(K).$$

Figure 3:
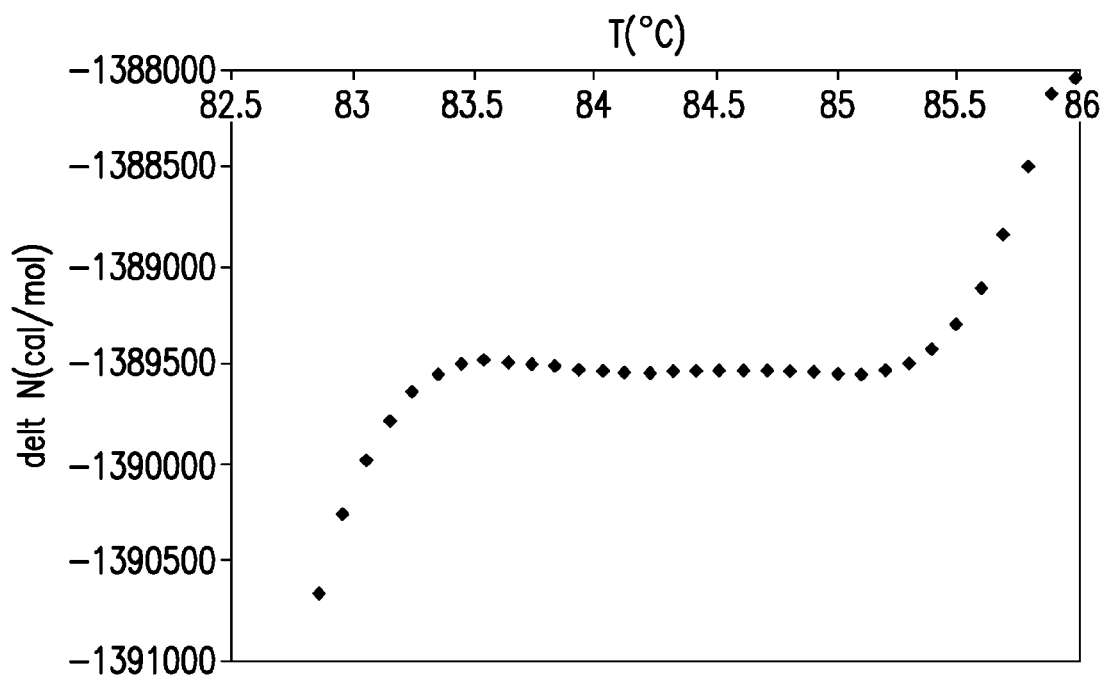
FIG. 3 illustrates the enthalpy domain that is calculated out of the melting curve of FIG. 1.
Figure 4:
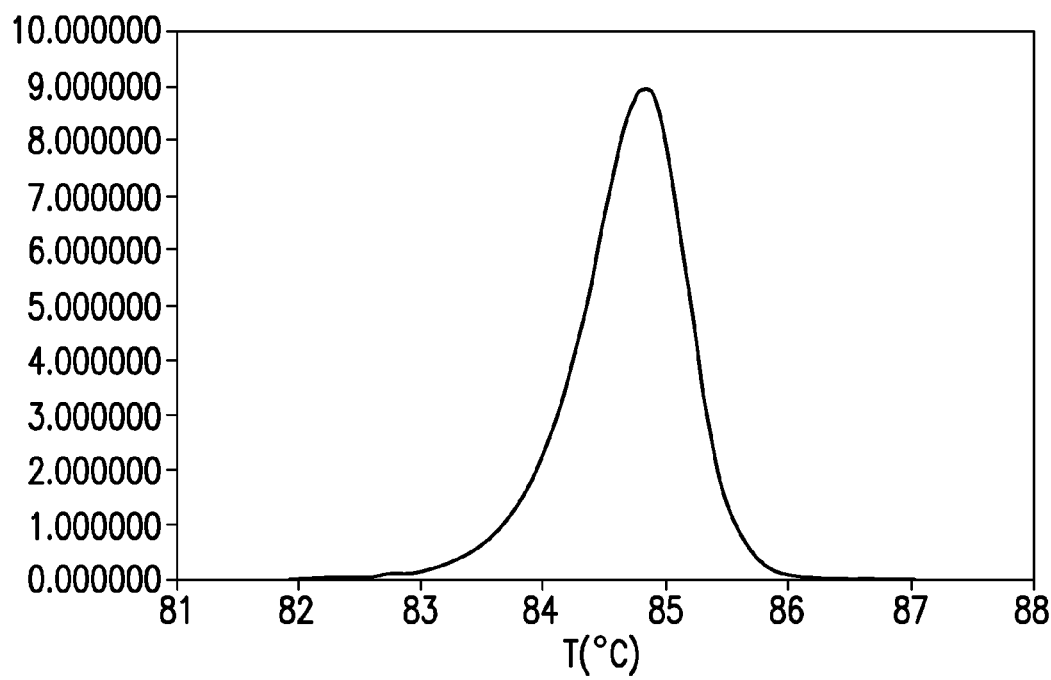
FIG. 4 illustrates a simulated melting curve that is derived from the calculated enthalpy and entropy.

An accurate enthalpy can be calculated based on this information. As illustrated in FIG. 3, the enthalpy domain that has been calculated from the melting curve of FIG. 1. Using the calculated enthalpy and entropy, the simulated derivative melting curve can be derived, as illustrated in FIG. 4.

Figure 5:
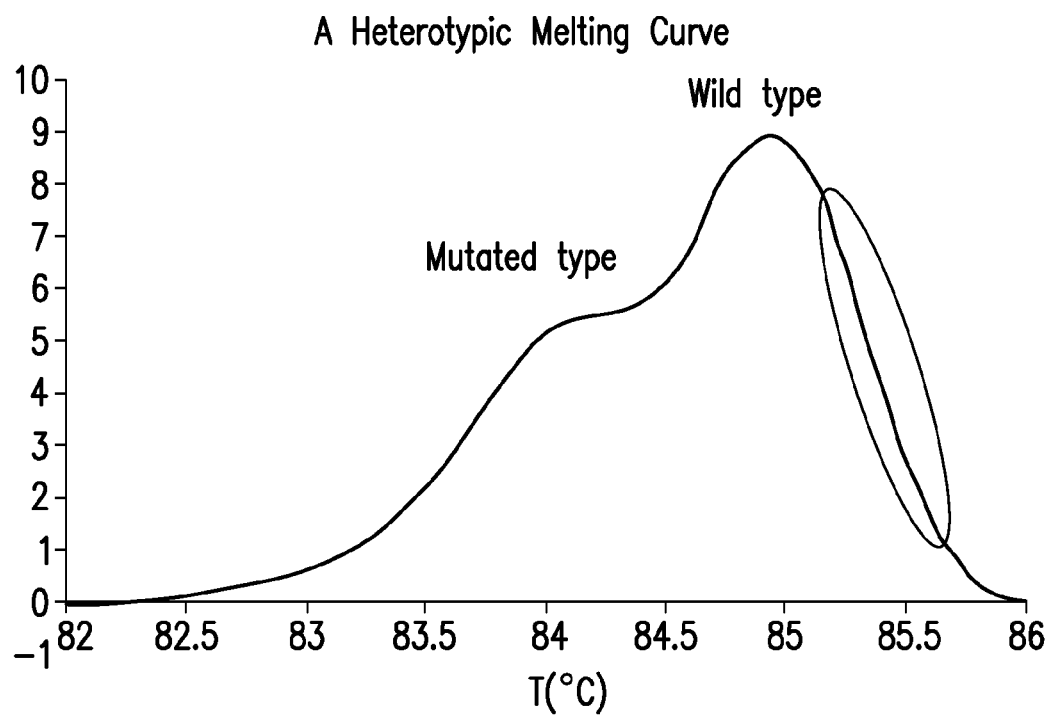
FIG. 5 illustrates a SNP melting curve in which the mutated melting curve for the mutant allele is overlapped with the melting curve for the wild type allele.
Figure 6:
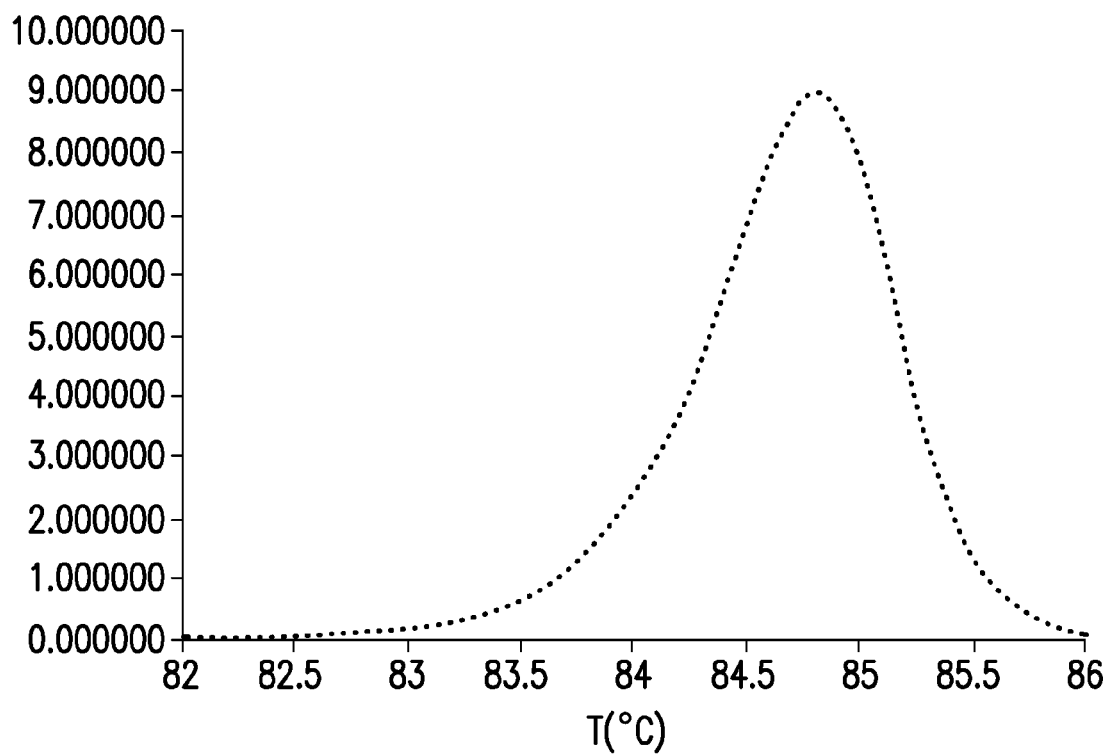
FIG. 6 illustrates a simulated melting curve for the wild type allele that is derived by using the non-overlapped part of melting curve for the wild type allele.
Figure 7:
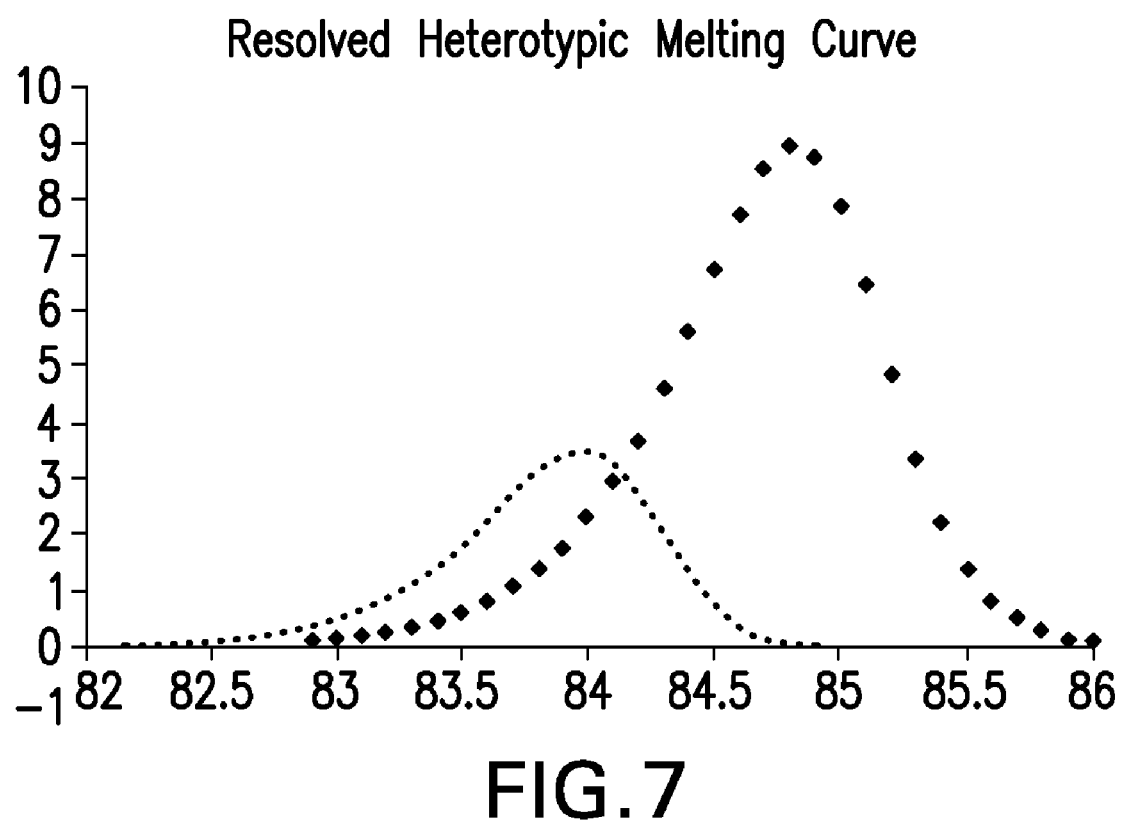
FIG. 7 illustrates a resolved melting curve for a mutant allele and a wild type allele.

FIG. 5 illustrates a SNP melting curve, wherein the mutated melting curve is overlapped with wild-type melting curve. In accordance with some aspects of the invention, by using the non-overlapped part of wild-type melting curve (shown as the circled region) and assuming that the entropy is consistent, the enthalpy can be calculated accurately. Therefore, the wild-type melting curve can then be derived, as illustrated in FIG. 6. By subtracting the wild-type melting curve from the SNP profile, the mutated type melting curve can then be derived. The resolved melting curve for the SNP is illustrated in FIG. 7, which shows the resolved heterotypic melting curve, i.e., the resolved wild-type melting curve and the resolved mutated-type melting curve. In one example, from the resolved SNP melting curve, the $T_m$ for the wild type is determined to be 84.78° C., and the $T_m$ for the mutated type is determined to be 83.9° C. The mutated DNA enthalpy and entropy can be calculated from the resolved melting curve.

The aspect of the invention is advantageous because it offers a method (i) to resolve SNP melting curves and precisely measure the melting temperature, (ii) for measuring DNA melting enthalpy and entropy from melting curve, and (iii) to figure out DNA sequence information from melting curve.

Thus, in accordance with a first aspect, the present invention provides a method for resolving a denaturation curve of a sample containing a first and second nucleic acid into a resolved denaturation curve for the first nucleic acid and a resolved denaturation curve for the second nucleic acid. In accordance with this aspect, the method comprises deriving a denaturation curve from denaturation data and calculating an estimated intrinsic physical value associated with the first nucleic acid by using data from a non-overlapping region of the denaturation curve. The method further comprises calculating a first resolved denaturation curve for the first nucleic acid using the estimated intrinsic physical value, and subtracting the first resolved denaturation curve for the first nucleic acid from the denaturation curve to generate a second resolved denaturation curve for the second nucleic acid.

In one embodiment, the denaturation data includes measurements of a quantifiable physical change P of the sample at a plurality of independent sample property points x. In another embodiment, the quantifiable physical change P is associated with denaturation of a nucleic acid. In a further embodiment, the plurality of independent sample property points x are a plurality of temperatures. In one embodiment, the intrinsic physical property is the enthalpy of denaturation of the first nucleic acid. In another embodiment, the method further comprises calculating the van't Hoff enthalpy of the first nucleic acid by using data from the non-overlapping region of the denaturation curve. In a further embodiment, the method further comprises the step of determining an estimated van't Hoff enthalpy and entropy change of the second nucleic acid from the resolved denaturation curve for the second nucleic acid.

In other embodiments, the method further comprises the step of determining the melting temperature of the first nucleic acid from the resolved melting curve for the first nucleic acid, and determining the melting temperature of the second nucleic acid from the resolved denaturation curve for the second nucleic acid. In another embodiment, the sample further includes a fluorescent dye for measuring the denaturation of the molecules in the sample. Suitable fluorescent dyes for detecting denaturation of molecules are well known in the art and include those described herein, such as the double-strand specific dyes of the Syber Green family of dyes and LCGreen Plus. Any suitable fluorescent dye can be used in the methods of the invention. In a further embodiment the quantifiable physical change is the fluorescence intensity. In one embodiment, the first nucleic acid and second nucleic acid are single nucleotide polymorphisms of one another. In another embodiment, the method further comprises the step of generating denaturation data including measurements of a quantifiable physical change P of the sample at a plurality of independent sample property points x for a sample. In a further embodiment, the quantifiable physical change P is associated with denaturation of a nucleic acid. In one embodiment, the denaturation data is thermal melt data.

Figure 8:
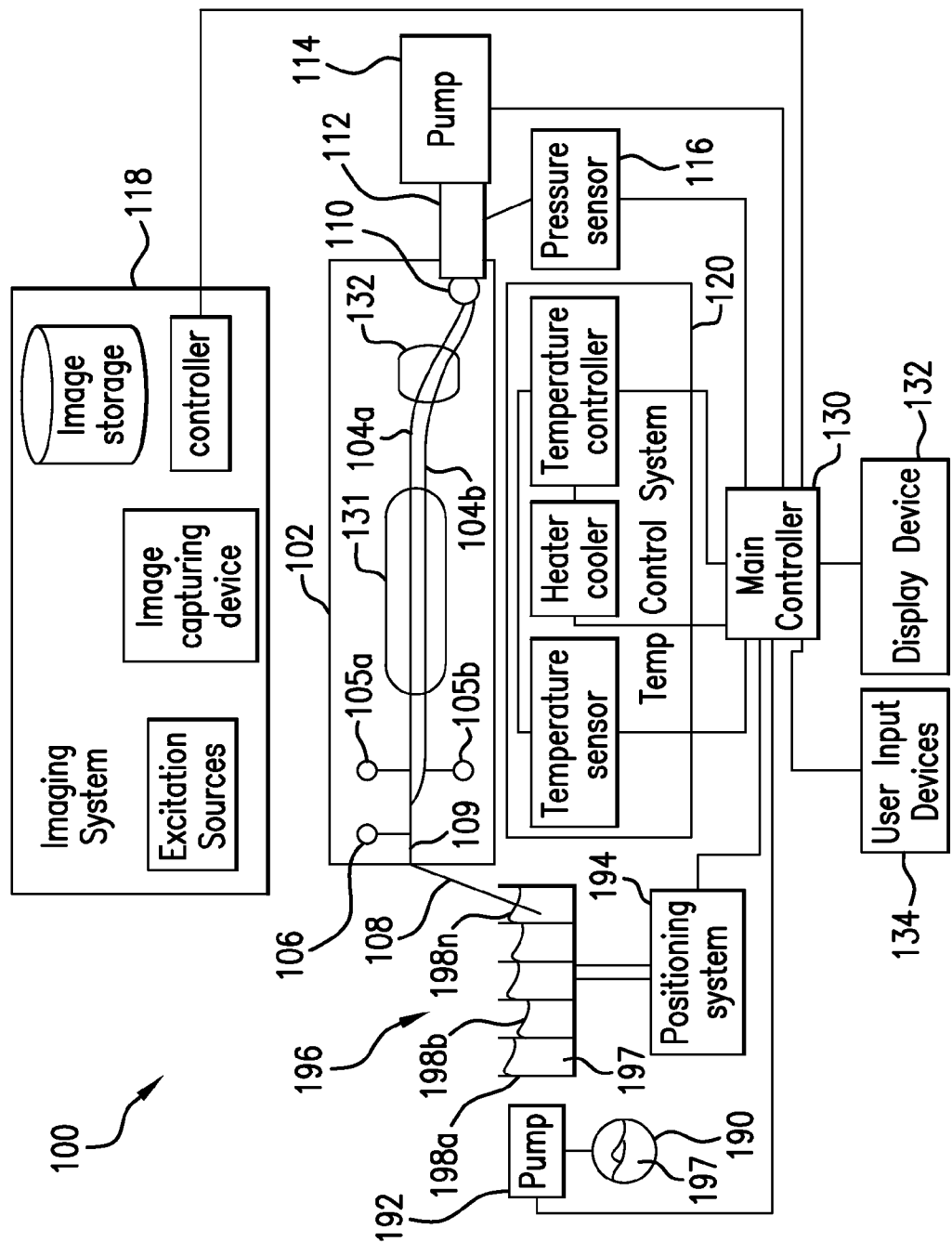
FIG. 8 illustrates a microfluidic device in accordance with some aspects of the present invention.

In a second aspect, the present invention also provides a system for resolving a denaturation curve of a sample containing a first and second nucleic acid into a resolved denaturation curve for the first nucleic acid and a resolved denaturation curve for the second nucleic acid. An example of a suitable system in accordance with some aspects of the invention is illustrated in connection with FIG. 8. As illustrated in FIG. 8, system 100 may include a microfluidic device 102. Microfluidic device 102 may include one or more microfluidic channels 104. In the examples shown, device 102 includes two microfluidic channels, channel 104a and channel 104b. Although only two channels are shown in the exemplary embodiment, it is contemplated that device 102 may have fewer than two or more than two channels. For example, in some embodiments, device 102 includes eight channels 104.

Device 102 may include two DNA processing zones, a DNA amplification zone 131 (a.k.a., PCR zone 131) and a DNA melting zone 132. A DNA sample traveling through the PCR zone 131 may undergo PCR, and a DNA sample passing through melt zone 132 may undergo high resolution thermal melting. As illustrated in FIG. 8, PCR zone 131 includes a first portion of channels 104 and melt zone 132 includes a second portion of channels 104, which is down stream from the first portion.

Device 102 may also include a sipper 108. Sipper 108 may be in the form of a hollow tube. Sipper 108 has a proximal end that is connected to an inlet 109 which inlet couples the proximal end of sipper 108 to channels 104. Device 102 may also include a common reagent well 106 which is connected to inlet 109. Device 102 may also include a locus specific reagent well 105 for each channel 104. For example, in the embodiment shown, device 102 includes a locus specific reagent well 105a, which is connected to channel 104a, and may include a locus specific reagent well 105b which is connected to channel 104b. Device 102 may also include a waste well 110 for each channel 104.

The solution that is stored in the common reagent well 106 may contain dNTPs, polymerase enzymes, salts, buffers, surface-passivating reagents, one or more non-specific fluorescent DNA detecting molecules, a fluid marker and the like. The solution that is stored in a locus specific reagent well 105 may contain PCR primers, a sequence-specific fluorescent DNA probe or marker, salts, buffers, surface-passivating reagents and the like.

In order to introduce a sample solution into the channels 104, system 100 may include a well plate 196 that includes a plurality of wells 198, at least some of which contain a sample solution (e.g., a solution containing a DNA sample). In the embodiment shown, well plate 196 is connected to a positioning system 194 which is connected to a main controller 130.

Main controller 130 may be implemented using a PXI-8105 controller which is available from National Instruments Corporation of Austin, Tex. Positioning system 194 may include a positioner (e.g., the MX80 positioner available from Parker Hannifin Corporation of PA ("Parker")) for positioning well plate 196, a stepping drive (e.g., the E-AC Microstepping Drive available from Parker) for driving the positioner, and a controller (e.g., the 6K4 controller available from Parker) for controlling the stepping drive.

To introduce a sample solution into the channels 104, the positioning system 194 is controlled to move well plate 196 such that the distal end of sipper 108 is submerged in the sample solution stored in one of the wells 198. FIG. 8 shows the distal end of 108 being submerged within the sample solution stored in well 198n.

In order to force the sample solution to move up the sipper and into the channels 104, a vacuum manifold 112 and pump 114 may be employed. The vacuum manifold 112 may be operably connected to a portion of device 102 and pump 114 may be operably connected to manifold 112. When pump 114 is activated, pump 114 creates a pressure differential (e.g., pump 114 may draw air out of a waste well 110), and this pressure differential causes the sample solution stored in well 198n to flow up sipper 108 and through inlet channel 109 into channels 104. Additionally, this causes the reagents in wells 106 and 105 to flow into a channel. Accordingly, pump 114 functions to force a sample solution and real-time PCR reagents to flow through channels 104. As illustrated in FIG. 8, melt zone 132 is located downstream from PCR zone 131. Thus, a sample solution will flow first through the PCR zone and then through the melting zone.

Referring back to well plate 196, well plate 196 may include a buffer solution well 198a. In one embodiment, buffer solution well 198a holds a buffer solution 197. Buffer solution 197 may comprise a conventional PCR buffer, such as a conventional real-time (RT) PCR buffer. Conventional PCR buffers are available from a number of suppliers, including: Bio-Rad Laboratories, Inc., Applied Biosystems, Roche Diagnostics, and others.

In order to achieve PCR for a DNA sample flowing through the PCR zone 131, the temperature of the sample must be cycled, as is well known in the art. Accordingly, in some embodiments, system 100 includes a temperature control system 120. The temperature control system 120 may include a temperature sensor, a heater/cooler, and a temperature controller. In some embodiments, a temperature control system 120 is interfaced with main controller 130 so that main controller 130 can control the temperature of the samples flowing through the PCR zone and the melting zone. Main controller 130 may be connected to a display device for displaying a graphical user interface. Main controller 130 may also be connected to user input devices 134, which allow a user to input data and commands into main controller 130.

To monitor the PCR process and the melting process that occur in PCR zone 131 and melt zone 132, respectively, system 100 may include an imaging system 118. Imaging system 118 may include an excitation source, an image capturing device, a controller, and an image storage unit. Other aspects of a suitable system in accordance with some aspects of the invention are disclosed in U.S. patent application Ser. No. 11/770,869, incorporated herein by reference in its entirety.

The system 100 further includes an appropriately controllable computer in communication with the user input devices 134, display device 132 and the main controller 130. The computer receives information from, among many sources, the imaging system 118 and temperature control system 120 and enables the identification of a nucleic acid in a sample including an unknown nucleic acid in accordance with some aspects of the invention.

In accordance with this second aspect, the system for resolving melt curves comprises a plotting module capable of plotting a denaturation curve from denaturation data and an estimating module capable of calculating an estimated intrinsic physical value associated with the first nucleic acid by using data from a non-overlapping region of a denaturation curve. The system further comprises a resolving module capable of calculating a resolved denaturation curve for the first nucleic acid using the estimated intrinsic physical value, and subtracting the first resolved denaturation curve for the first nucleic acid from a denaturation curve to generate a second resolved denaturation curve for the second nucleic acid.

In accordance with this embodiment, the plotting module comprises software stored on a computer readable medium (e.g., a non-volatile storage device or other storage device), where the software is configured such that when executed by a computer, the software enables the computer to plot a denaturation curve from denaturation data. In one embodiment, the estimating module comprises software stored on a computer readable medium (e.g., a non-volatile storage device or other storage device), where the software is configured such that when executed by a computer, the software enables the computer to calculate an estimated intrinsic physical value associated with the first nucleic acid by using data from a non-overlapping region of a denaturation curve. In other embodiments, the resolving module comprises software stored on a computer readable medium (e.g., a non-volatile storage device or other storage device), where the software is configured such that when executed by a computer, the software enables the computer to calculate a resolved denaturation curve for the first nucleic acid using the estimated intrinsic physical value, and subtracting the first resolved denaturation curve for the first nucleic acid from a denaturation curve to generate a second resolved denaturation curve for the second nucleic acid.

In one embodiment, the denaturation data includes measurements of a quantifiable physical change P of the sample at a plurality of independent sample property points x. In another embodiment, the quantifiable physical change P is associated with the denaturation of a nucleic acid. In a further embodiment, the plurality of independent sample property points x are a plurality of temperatures. In one embodiment, the intrinsic physical property is the enthalpy of denaturation of the first nucleic acid. In another embodiment, the estimating module is further capable of calculating the van't Hoff enthalpy of the first nucleic acid by using data from the non-overlapping region of the denaturation curve. In a further embodiment, the system further comprises a thermodynamic information determining module capable of determining an estimated van't Hoff enthalpy and entropy change of the second nucleic acid from the second resolved denaturation curve for the second nucleic acid.

In another embodiment, the system further comprises a melting temperature determining module capable of determining the melting temperature of the first nucleic acid from the resolved denaturation curve for the first nucleic acid, and determining the melting temperature of the second nucleic acid from the resolved denaturation curve for the second nucleic acid. In one embodiment, the melting temperature determining module comprises software stored on a computer readable medium (e.g., a non-volatile storage device or other storage device), where the software is configured such that when executed by a computer, the software enables the computer to measure temperature at the derivative peak of the melting curve.

In other embodiments, the sample further includes a fluorescent dye for measuring the denaturation of the molecules in the sample. Suitable fluorescent dyes for detecting denaturation of molecules are well known in the art and include those described herein, such as the double-strand specific dyes of the Syber Green family of dyes and LCGreen Plus. Any suitable fluorescent dye can be used in the methods of the invention.

In further embodiments, the system further comprises a generating unit capable of generating denaturation data including measurements of a quantifiable physical change P of the sample at a plurality of independent sample property points x for a sample. In one embodiment, the generating unit comprises software stored on a computer readable medium (e.g., a non-volatile storage device or other storage device), where the software is configured such that when executed by a computer, the software enables the computer to generate denaturation data including measurements of a quantifiable physical change P of the sample at a plurality of independent sample property points x for a sample. In a further embodiment, the quantifiable physical change P is associated with denaturation of a nucleic acid. In one embodiment, the denaturation data is thermal melt data.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of resolving a denaturation curve of a sample containing a first and second nucleic acid into a resolved denaturation curve for the first nucleic acid and a resolved denaturation curve for the second nucleic acid, said method comprising:
    (a) deriving a denaturation curve from denaturation data;
    (b) calculating an estimated intrinsic physical value associated with the first nucleic acid by using data from a non-overlapping region of the denaturation curve;
    (c) calculating a first resolved denaturation curve for the first nucleic acid using the estimated intrinsic physical value; and
    (d) subtracting the first resolved denaturation curve for the first nucleic acid from the denaturation curve to generate a second resolved denaturation curve for the second nucleic acid.

2. The method of claim 1, wherein the denaturation data includes measurements of a quantifiable physical change P of the sample at a plurality of independent sample property points x, wherein the quantifiable physical change P is associated with denaturation of a nucleic acid.

3. The method of claim 2, wherein the plurality of independent sample property points x are a plurality of temperatures.

4. The method of claim 3, wherein the intrinsic physical property is the enthalpy of denaturation of the first nucleic acid.

5. The method of claim 4, further comprising calculating the van't Hoff enthalpy of the first nucleic acid by using data from the non-overlapping region of the denaturation curve.

6. The method according to claim 5, further comprising the step of determining an estimated van't Hoff enthalpy and entropy change of the second nucleic acid from the resolved denaturation curve for the second nucleic acid.

7. The method according to claim 1, further comprising the step of determining a melting temperature of the first nucleic acid from the resolved melting curve for the first nucleic acid.

8. The method of claim 1, further comprising the step of determining a melting temperature of the second nucleic acid from the resolved denaturation curve for the second nucleic acid.

9. The method according to claim 2, wherein said sample further includes a double-strand specific fluorescent dye, and wherein said quantifiable physical change is the fluorescence intensity.

10. The method according to claim 1, wherein the first nucleic acid and second nucleic acid are single nucleotide polymorphisms of one another.

11. The method according to claim 1 further comprising the step of generating denaturation data including measurements of a quantifiable physical change P of the sample at a plurality of independent sample property points x for a sample, wherein the quantifiable physical change P is associated with denaturation of a nucleic acid.

12. The method according to claim 1, wherein the denaturation data is thermal melt data.

13. A system for resolving a denaturation curve of a sample containing a first nucleic acid and a second nucleic acid into a resolved melt curve for the first nucleic acid and a resolved melt curve for the second nucleic acid, said system comprising:
    (a) a plotting module capable of plotting a denaturation curve from denaturation data;
    (b) an estimating module capable of calculating an estimated intrinsic physical value associated with the first nucleic acid by using data from a non-overlapping region of a denaturation curve; and
    (c) a resolving module capable of calculating a resolved denaturation curve for the first nucleic acid using the estimated intrinsic physical value, and subtracting the first resolved denaturation curve for the first nucleic acid from a denaturation curve to generate a second resolved denaturation curve for the second nucleic acid.

14. The system of claim 13, wherein the denaturation data includes measurements of a quantifiable physical change P of the sample at a plurality of independent sample property points x, wherein the quantifiable physical change P is associated with the denaturation of a nucleic acid.

15. The system of claim 14, wherein said estimating module is further capable of calculating the van't Hoff enthalpy of the first nucleic acid by using data from the non-overlapping region of the denaturation curve.

16. The system of claim 15, further comprising a thermodynamic information determining module capable of determining an estimated van't Hoff enthalpy and entropy change of the second nucleic acid from the second resolved denaturation curve for the second nucleic acid.

17. The system of claim 13, further comprising a melting temperature determining module capable of determining the melting temperature of the first nucleic acid from the resolved denaturation curve for the first nucleic acid.

18. The system of claim 13, further comprising a melting temperature determining module capable of determining the melting temperature of the second nucleic acid from the resolved denaturation curve for the second nucleic acid.

* * * * *